(12) United States Patent
Rigoutsos et al.

(10) Patent No.: US 7,698,067 B2
(45) Date of Patent: Apr. 13, 2010

(54) SEQUENCE PATTERN DESCRIPTORS FOR TRANSMEMBRANE STRUCTURAL DETAILS

(75) Inventors: Isidore Rigoutsos, Astoria, NY (US); Peter Riek, West Pennant Hills (AU); Robert M. Graham, Pymble (AU); Jiri Novotny, Fairlight (AU)

(73) Assignee: International Business Machines Corporation, Armonk, NY (US)

( * ) Notice: Subject to any disclaimer, the term of this patent is extended or adjusted under 35 U.S.C. 154(b) by 293 days.

(21) Appl. No.: 10/305,552

(22) Filed: Nov. 27, 2002

(65) Prior Publication Data

US 2003/0157524 A1 Aug. 21, 2003

Related U.S. Application Data

(60) Provisional application No. 60/356,439, filed on Feb. 12, 2002.

(51) Int. Cl.
*G01N 33/48* (2006.01)
*G01N 31/00* (2006.01)
*G06G 7/48* (2006.01)

(52) U.S. Cl. .............................. 702/19; 702/27; 703/11

(58) Field of Classification Search .................. 702/19, 702/20; 435/6
See application file for complete search history.

(56) References Cited

U.S. PATENT DOCUMENTS 5,948,887 A * 9/1999 Evans et al. ................. 530/333
2002/0146724 A1* 10/2002 Toll et al. ........................ 435/6

OTHER PUBLICATIONS

Frishman et al. "Knowledge-Based Protein Secondary Structure Assignment" Proteins: Structure, Function, and Genetics (1995) vol. 23, pp. 566-579.*

Ginalksi et al. "Practical Lessons From Protein Structure Prediction" (2005) vol. 33, pp. 1874-1891.*
Altschul et al., "Gapped BLAST and PSI-BLAST: A New Generation of Protein Database Search Programs," Nucleic Acids Research, vol. 25, No. 17, pp. 3389-3402 (1997).
Bairoch et al., "The SWISS-PROT Protein Sequence Database and its Supplement TrEMBL in 2000," Nucleic Acids Research, vol. 28, No. 1, pp. 45-48, (2000).
Karplus et al., "Hidden Markov Models for Detecting Remote Protein Homologies," Bioinformatics, vol. 14, No. 10, pp. 846-856 (1998).
Popot et al., "Helical Membrane Protein Folding, Stability, and Evolution," Ann. Rev. Biochem., 68:881-922 (2000).
Riek et al., "Non-α-Helical Elements Modulate Polytopic Membrane Protein Architecture," J. Mol. Biol., 306, pp. 349-362 (2001).
Rigoutsos et al., "Combinational Pattern Discovery in Biological Sequences: the TEIRESIAS Algorithm," Bioinformatics, vol. 14, No. 1, pp. 55-67 (1998).
Rigoutsos et al., "Dictionary Building Via Unsupervised Hierarchical Motif Discovery in the Sequence Space of Natural Proteins," Proteins: Structure, Function, and Genetics, 37:264-277 (1999).
Rigoutsos et al., "Dictionary-Driven Protein Annotation," Nucleic Acids Research, vol. 30, No. 17, pp. 3901-3916 (2002).
Ubarretxena-Belandia et al., "Helical Membrane Proteins: Diversity of Functions in the Context of Simple Architecture," Current Opinion in Structural Biology, 11:370-376 (2001).

* cited by examiner

*Primary Examiner*—Eric S DeJong
(74) *Attorney, Agent, or Firm*—Ryan, Mason & Lewis, LLP

(57) ABSTRACT

The relationship between an amino acid sequence of a protein and its three-dimensional structure is at the very core of structural biology and bioinformatics. The occurrence and conservation of non-canonical conformations is a "local" phenomenon, i.e., non-canonical conformations are encoded intra-helically by short peptide sequences (heptapeptides at most). Effective descriptors can be formed for these short sequences employing training sets. Multiple, distinct patterns are created representing these sequences. A composite descriptor is formed by selecting from among the patterns discovered. The composite descriptor has a high level of sensitivity and specificity while, at the same time, a boosted signal-to-noise ratio.

12 Claims, 4 Drawing Sheets

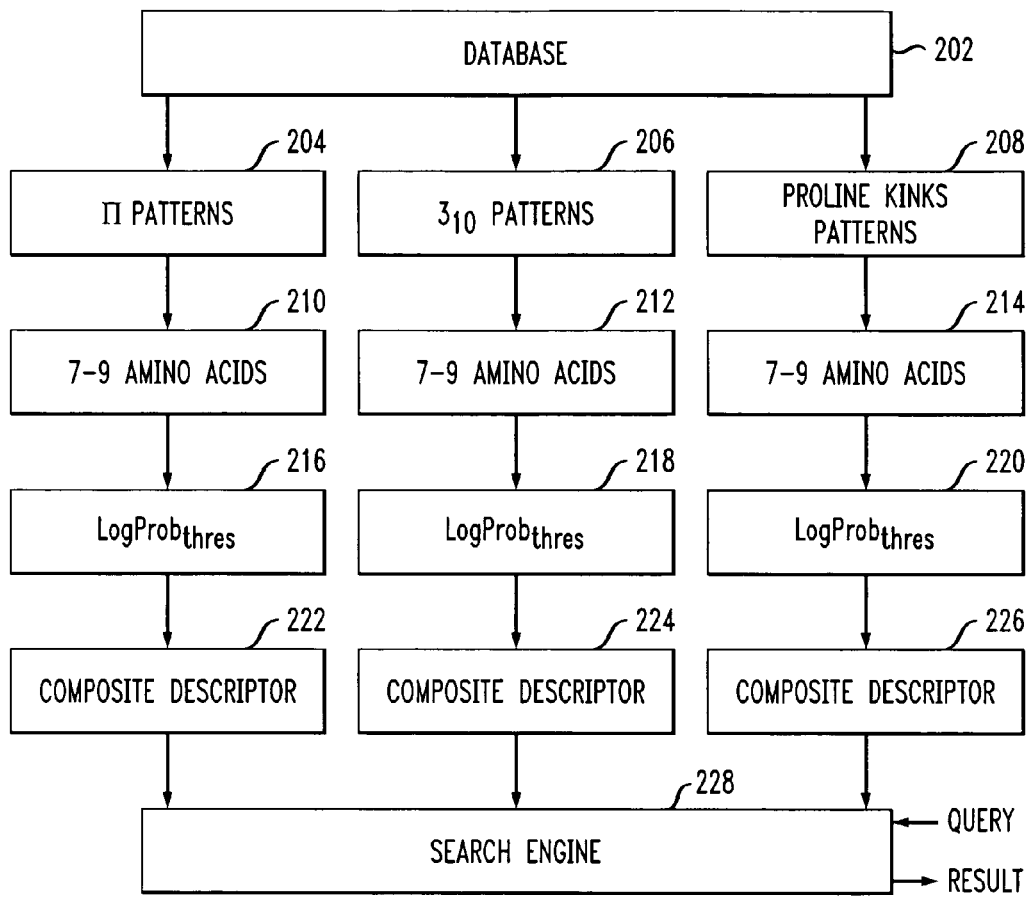
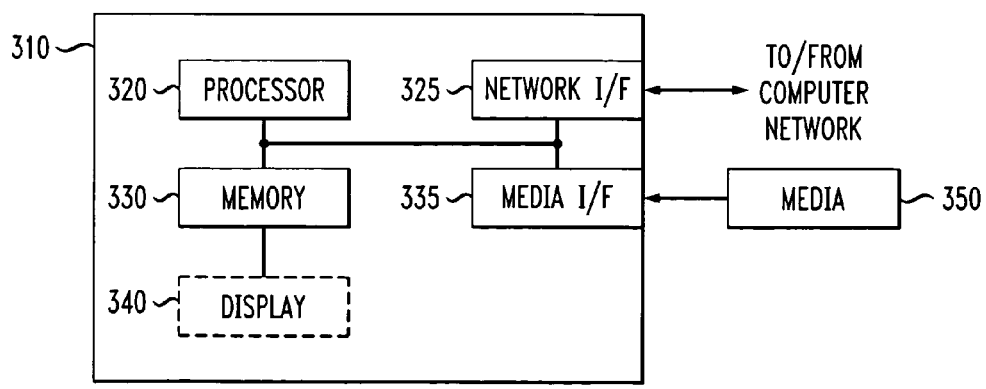

SEQUENCE LISTING

<160> NUMBER OF SEQ ID NOS: 2

<210> SEQ ID NO 1
<211> LENGTH: 6
<212> TYPE: PRT
<213> ORGANISM: Unknown
<220> FEATURE:
<223> OTHER INFORMATION: Exemplary Pattern for Illustrating the
      Techniques
<220> FEATURE:
<221> NAME/KEY: MISC_FEATURE
<222> LOCATION: (1)..(1)
<223> OTHER INFORMATION: Xaa is any one of Lys or Arg
<220> FEATURE:
<221> NAME/KEY: MISC_FEATURE
<222> LOCATION: (2)..(2)
<223> OTHER INFORMATION: Xaa is any naturally occurring amino acid
<220> FEATURE:
<221> NAME/KEY: MISC_FEATURE
<222> LOCATION: (4)..(4)
<223> OTHER INFORMATION: Xaa is any one of Ile, Leu, Met, or Val
<220> FEATURE:
<221> NAME/KEY: MISC_FEATURE
<222> LOCATION: (5)..(5)
<223> OTHER INFORMATION: Xaa is any one of Ala or Gly

<400> SEQUENCE: 1

Xaa Xaa Lys Xaa Xaa Leu
1               5

<210> SEQ ID NO 2
<211> LENGTH: 348
<212> TYPE: PRT
<213> ORGANISM: Bovine Rhodopsin

<400> SEQUENCE: 2

Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp Gln Phe Ser Met Leu Ala Ala Tyr Met Phe Leu Leu Ile
        35                  40                  45

Met Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Val Gly Trp Ser
                165                 170                 175

Arg Tyr Ile Pro Glu Gly Met Gln Cys Ser Cys Gly Ile Asp Tyr Tyr
            180                 185                 190

Thr Pro His Glu Glu Thr Asn Asn Glu Ser Phe Val Ile Tyr Met Phe

-continued

```
            195                 200                 205
Val Val His Phe Ile Ile Pro Leu Ile Val Ile Phe Phe Cys Tyr Gly
    210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Leu Pro Tyr Ala Gly Val Ala
                260                 265                 270

Phe Tyr Ile Phe Thr His Gln Gly Ser Asp Phe Gly Pro Ile Phe Met
            275                 280                 285

Thr Ile Pro Ala Phe Phe Ala Lys Thr Ser Ala Val Tyr Asn Pro Val
    290                 295                 300

Ile Tyr Ile Met Met Asn Lys Gln Phe Arg Asn Cys Met Val Thr Thr
305                 310                 315                 320

Leu Cys Cys Gly Lys Asn Pro Leu Gly Asp Asp Glu Ala Ser Thr Thr
                325                 330                 335

Val Ser Lys Thr Glu Thr Ser Gln Val Ala Pro Ala
                340                 345
```

SEQUENCE PATTERN DESCRIPTORS FOR TRANSMEMBRANE STRUCTURAL DETAILS

CROSS REFERENCE TO RELATED APPLICATIONS

This application claims the benefit of U.S. Provisional Application No. 60/356,439, filed Feb. 12, 2002.

FIELD OF THE INVENTION

The present invention relates generally to sequence detection and, more particularly, to methods and apparatus for identifying structural details in transmembrane proteins through the comparison of a query sequence to composite pattern descriptors.

BACKGROUND OF THE INVENTION

The relationship between the amino acid sequence of a protein and its three-dimensional structure is at the very core of structural biology and bioinformatics. Although much structural data on proteins has been collected, there remains a need for a general algorithm for deducing the folding of a protein, i.e., its three-dimensional structure, from its amino acid sequence. Some successful approaches to predicting the three-dimensional structure and function of proteins have been based on the fact that the primary protein structures of a large number of proteins is currently known, and based on similarities, are organized into a fewer number of groups, or families. Proteins within the same family are presumed to share the same three-dimensional structure.

Proteins, or polypeptides, are amphiphilic polymers containing a mixture of polar and non-polar side chains. This physical property places an upper limit, of approximately 300-400 amino acid residues, on the size of individual folded regions of a protein, called domains. Thus, only a few thousand unique folds within the domain regions are expected to occur naturally. Folding refers to the secondary structure of the proteins, i.e., α-helices, β-sheets and loops. Conservation of the three-dimensional structure of a protein, e.g., secondary or tertiary, typically correlates to conserved regions of the amino acid sequence defining the primary protein structure. Such conserved regions of the sequence are termed "signature" sequences as they signify a given three-dimensional structure.

The identification of these signature sequences is often conducted using similarity search software, such as the FASTA, BLAST/PSI-BLAST, and Smith-Waterman programs. Such similarity search software programs conduct direct pair-wise comparisons of a query sequence with every sequence present in a database. Alternatively, conserved sequence patterns in a set of multiple aligned sequences may be identified. If enough multiple aligned sequences are available, they can be used to build a Markov model and a search engine suitable for searching databases looking for more instances of similar patterns.

The pattern discovery algorithm, Teiresias, has been used to identify and build a very large collection of sequence patterns, or seqlets, by processing the GenPept database as a whole (the process is also routinely repeated at regular intervals on increasingly larger installments of the SwissProt/TrEMBL database). For a discussion of the Teiresias algorithm, see, for example, Floratos, et al., U.S. Pat. No. 6,108,666, "Methods and Apparatus for Pattern Discovery in 1-Dimensional Systems"; Floratos, et al., U.S. Pat. No. 6,092,065, "Methods and Apparatus for Discovery, Clustering and Classification of Patterns in 1-Dimensional Event Streams"; Rigoutsos, I. and A. Floratos, "Combinatorial Pattern Discovery in Biological Sequences: the Teiresias Algorithm," Bioinformatics, 14(1):55-67, 1998; and Rigoutsos, I. and A. Floratos, "Motif Discovery Without Alignment Or Enumeration," Proceedings 2nd Annual ACM International Conference on Computational Molecular Biology, New York, NY, March 1998, the disclosures of which are incorporated by reference herein. Generally, each sequence pattern is a string of literals interspersed with zero or more "wild-cards." The location of each literal can be occupied by either a unique amino acid or a small set of permitted amino acids, whereas the location of each of the wild cards can be occupied by any amino acid. Take for example the pattern [SEQ. ID. NO. 1]: {KR}.K{ILMV}{AG}L, wherein each literal is shown bracketed, and each wild card position is represented by the symbol ".". This particular pattern describes all hexapeptides that begin with either a lysine or an arginine, followed by any one of the 20 amino acids, followed by a lysine, followed by any one of {isoleucine, leucine, methionine, valine}, followed by any one of {alanine, glycine} and finally a leucine.

The patterns contained in this collection, known as the Bio-Dictionary, have been found to identify structural and functional properties that cross protein family boundaries. The Bio-Dictionary pattern collection nearly completely covers the currently known sequence space of natural proteins and can thus be used in lieu of the original sequence database for applications such as similarity searching, protein annotation, and gene finding.

The transmembrane helices of polytopic proteins are common building elements of many large, biologically important structures, such as tissue-specific or ligand-specific receptors (or both) and enzymes. Non-canonical conformations occur frequently in these helices and are critical determinants of their structure and function. Unfortunately, the structural study of such proteins has been hindered by the inability of researchers to successfully crystallize samples for analysis. Observing the three-dimensional structure of these non-canonical regions has been a challenge. Recent focus has shifted to the analysis of amino acid sequences, i.e., the primary structure of these proteins, when it was discovered that the non-canonical conformations and the respective sequences encoding them are often conserved. However, the sequences encoding non-canonical conformations are generally only a few amino acid residues in length. Thus, traditional approaches using sequence similarity tools or Markov models are ineffective as are the traditional secondary structure prediction methods (e.g., some of the public prediction servers suggested a β structure in place of a helical kink). It is thus beneficial to have a method for analyzing polytopic proteins, specifically non-canonical conformations within those proteins from the primary protein structure.

SUMMARY OF THE INVENTION

The present invention provides solutions to the above and other needs by providing improved techniques for identifying non-canonical protein conformations, as will be described in greater detail below. A computer-based method for identifying regions in a query sequence corresponding to non-canonical protein conformations comprises the steps of forming a composite pattern descriptor for sequence patterns corresponding to instances of non-canonical protein conformations; and using the composite pattern descriptor to identify positions of a query sequence corresponding to the sequence patterns. The sequence patterns may comprise amino acid sequence patterns, nucleotide sequence patterns or both.

The composite pattern descriptor is formed, for example, by constructing a set of sequence patterns from a set of sequence fragments, the sequence fragments corresponding to instances of non-canonical conformations; and selecting sequence patterns for a plurality of non-canonical conformations. The sequence fragments may comprise amino acid sequence fragments, nucleotide sequence fragments, or both.

The present invention is directed to non-canonical protein conformations within transmembrane α-helices, including, but not limited to, π-like helices, $3_{10}$-like helices and proline-induced kinks. The present invention recognizes that deducing fine details of the α-helical structure based on knowledge of these non-canonical protein conformations allows for the prediction of local three-dimensional structures within the protein from the sequence itself. Thus, the inability to study the three-dimensional structure of transmembrane proteins, due to the difficulty in crystallizing samples, may in part be overcome by elucidating the fine detailed structure of the α-helices spanning the membrane.

A more complete understanding of the present invention, as well as further features and advantages of the present invention, will be obtained by reference to the following detailed description and drawings.

BRIEF DESCRIPTION OF THE DRAWINGS

FIG. 2 is a block diagram of a composite descriptor system according to one embodiment of the present invention;

FIG. 3 is a block diagram of an exemplary hardware implementation of a descriptor system of the present invention;

DETAILED DESCRIPTION OF PREFERRED EMBODIMENTS

Of particular interest are three non-canonical conformations of transmembrane α-helices, namely, π-like helices, $3_{10}$-like helices and proline-induced kinks. Some general sequence features are known about non-canonical structures and their encoding sequences. For example, in π-like helices, residues with large aromatic or hydrophobic side-chains often precede proline residues, $3_{10}$-like helices typically contain β-branched side-chains N-terminal to any proline residues and, in proline-induced kinks, aromatic residues with glycine are frequently present near the kinks.

Helical geometric properties are typically described by their backbone torsional values Φ, Ψ, as illustrated in Table 1, below. However, the relationship of the torsion to chain geometries of non-canonical conformations is complex and degenerate, i.e., many different combinations of Φ, Ψ values are compatible with a single α-carbon ($C_\alpha$) trace. More complex geometry descriptors of different helical conformations include $C_\alpha$-$C_\alpha$ distances (plotted as differences from the corresponding values in a canonical α-helix), helical wheel (spoke angle) plots, rise per residue plots, and H-bond connectivity plots. Table 1 summarizes the geometric properties of π-like helices and $3_{10}$-like helices as compared to α-helices and includes parameters such as rise per residue.

Figures 1A, 1B, 1C:
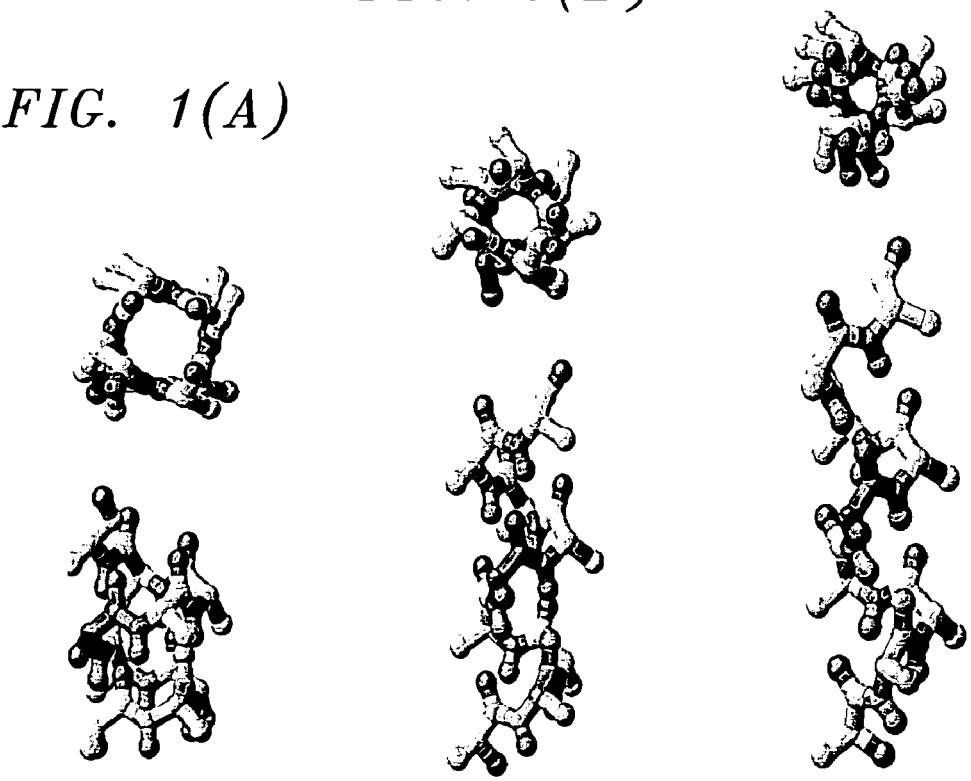
FIGS. 1(A)-(C) show molecular representations of helical conformations.

FIGS. 1(A)-(C) show molecular representations of three helical conformations. FIG. 1(A) shows a π-like helix, FIG. 1(B) shows an α-helix and FIG. 1(C) shows a $3_{10}$-like helix. Variations in the conformations of each of the helices pictured can best be identified by studying each helical representation in conjunction with the top-down view presented directly above each helical representation. For example, the $3_{10}$-like helix pictured in FIG. 1(C) has three amino acid residues per turn of the helix, thus resulting in a tightly wound conformation.

TABLE 1

| Helix type | | π | α | $3_{10}$ |
|---|---|---|---|---|
| IUPAC code | | $4.4_{16}$ | $3.6_{13}$ | $3.0_{10}(3.2_{10})$ |
| B   t | | | | |
| a   o | | | | |
| c   r | Φ | −57° | −57°(−62°) | −71° |
| k   s | | | | |
| b   i | | | | |
| o   o | | | | |
| n   n | Ψ | −70° | −47°(−41°) | −16° |
| e   s | | | | |
| Residues per turn | | 4.4 | 3.6 | 3.0(3.2) |
| Rise per residue [Å] | | 1.0 | 1.6 | 1.9 |
| Inter-residue angle | | 86° | 100°(102°) | 120°(112°) |
| Helical radius [Å] | | 2.8 | 2.3 | 1.9 |

Deduction of the α-helical structure based on knowledge of these non-canonical protein conformations allows for the prediction of the three-dimensional structure of the protein from the sequence itself. Thus, the inability to study the three-dimensional structure of transmembrane proteins, due to the difficulty in crystallizing samples, may in part be overcome by elucidating the fine detailed structure of the α-helices spanning the membrane.

FIG. 2 is a block diagram of a composite descriptor system 200 according to one embodiment of the present invention. The use of composite descriptors to identify non-canonical conformations involves first constructing a set of sequence patterns from a small and carefully constructed database 202 of sequence fragments. Composite descriptors may be formed and used according to the method outlined in U.S. patent application Ser. No. 09/712,638, filed Nov. 14, 2000, entitled "Unsupervised Building and Exploitation of Composite Descriptors," incorporated herein by reference. The sequence fragments and the constructed sequence patterns may include either amino acid sequence fragments and patterns, nucleotide sequence fragments and patterns, any other sequence indicative of non-canonical protein conformations or any combinations of the aforementioned sequences. The database 202 maybe embodied, for example, as a collection of all the sequence fragments encoding non-canonical conformations, derived from analysis of transmembrane helices sequence fragments that have been deposited in the Brookhaven Data Bank, a commercial database. The collection can be kept up-to-date with the sequences being deposited in the Brookhaven Data Bank. In an exemplary embodiment, the current collection contains 34 sequence fragments of π-like helical motifs, 33 sequence fragments of $3_{10}$-like helical motifs, and 53 sequence fragments of proline- and non-proline-induced kink motifs. The amino acid sequence fragments correspond to π-like helices, $3_{10}$-like helices, and proline-induced kinks. For each of the three non-canonical conformations, an extensive set of sequence patterns 204, 206 and 208 is computed. Each pattern, by virtue of the fact that it is a pattern, occurs at least twice in database 202. In one embodiment, the Teiresias algorithm is used to separately compute sequence patterns for each non-canonical conformation category in the database 202. The sequence fragments within each category preferably include at least one signature residue. A signature residue is an amino acid residue which is characteristic of the conformation, i.e., the proline for proline-induced kinks. Most preferably, only those patterns derived from sequence fragments with a residue at a certain fixed position, matching a signature residue, are selected. While computing the sequence patterns, amino acids in each of the following classes are permitted to replace one another: {A,G}, {D,E}, {K,R}, {I,L,M,V}, {S,T}, {Q,N} and {F,Y}.

The patterns 204, 206 and 208, derived from database 202, are then further processed. First, all wild card positions appearing in the patterns are replaced by a regular expression of the type $\{X_1 X_2 \ldots X_N\}$ wherein each $X_i$ is an amino acid residue that the wild card represents. N represents a maximal number of amino acid residues. Any patterns wherein the number of amino acid residues is greater than or equal to N are discarded. For example, if N equals seven, then all patterns wherein N is greater than or equal to seven are discarded. Second, any single literal present in the patterns is replaced by the respective classes, which were highlighted above. For example, the single literal A is replaced by {AG}, G by {AG}, D by {DE} and so forth.

For each set of patterns 204, 206 and 208, only those patterns containing between seven and nine positions inclusive are selected and retained as patterns 210, 212 and 214, respectively. Thus, the pattern [SEQ.ID. NO. 1]: {KR}.K{ILMV}{AG}L, representing a hexapeptide, would not be retained. From patterns 210, 212 and 214, only those patterns having a predetermined estimated log-probability of being an accidental, random appearance, are retained as patterns 216, 218 and 220, respectively. The predetermined estimated log-probability may vary according to the level of sensitivity desired. Preferably, the estimated log-probability is less than or equal to −23. The estimated log-probability for each pattern is computed using a $2^{nd}$-order Markov chain built from the contents of the Swissprot/TrEMBL database. For a discussion of the procedure for computing the estimated log-probability, see, for example, R. Durbin et al., "Biological Sequence Analysis," Cambridge University Press, 1998. Choosing this parameter allows for the accuracy and the sensitivity of the system to be set.

Those $N_i$ patterns that satisfy the above properties are included in a composite descriptor $C_i$ for the ith category, wherein i∈{π-like helices, $3_{10}$-like helices and proline-induced kinks}. Thus, composite descriptor 222 is formed for π-like helices, composite descriptor 224 is formed for $3_{10}$-like helices and composite descriptor 226 is formed for proline-induced kinks. The number of patterns for which each of composite descriptor 222, 224 and 226 is formed is further limited by a probability value, such as the user-defined LogProb$_{thres}$. For example, given the current collection of sequence fragments, when the LogProb$_{thres}$ equals −25, composite descriptor 222, for π-like helices, is formed for 5814 patterns, composite descriptor 224, for $3_{10}$-like helices, is formed for 4250 patterns, and composite descriptor 226, for proline-induced kinks, is formed for 11282 patterns.

In a preferred embodiment, composite descriptors 222, 224 and 226 are combined into a search engine 228 that can process an amino acid query sequence and produce various annotated regions of the sequence corresponding to instances of non-canonical conformation(s). The patterns from search engine 228 which match regions of the query, assign "an amount" to the rightmost $R_i$ positions of the region of the query sequence. The amount is equal to $1/N_i$, so as to account for the fact that each descriptor is formed for a different number of patterns. To screen out non-positive or low positive query positions, a particular position will be considered further, if and only if, it was matched by at least P patterns. It is to be understood that any combination of composite descriptors 222, 224 and 226, and likewise, the use of each descriptor individually, may be made without departing from the scope of the invention.

The sensitivity of and the potential to generate "cross-talk" for each of composite descriptors 222, 224 and 226 may be evaluated by processing the peptide sequences of three 30 non-redundant training sets. Cross-talk, if present, would demonstrate itself when one or more patterns from the composite descriptor for a type i non-canonical conformation matched training set instances for a type j conformation, with i different from j (here, i and j ∈{π-like helices, $3_{10}$-like helices and proline-induced kinks}). In tests run using composite descriptors exemplary of composite descriptor 222, 224 and 226, none of the composite descriptors identified training set instances outside of their own conformation. Thus, the tests indicated that there is no cross-talk between the composite descriptors of the present invention.

The rate at which false positives are generated by the system may be determined by interrogating an appropriate database of canonical sequences simultaneously with composite descriptor 222, 224 and 226. In a test run to determine the rate at which false positives are generated by the system, a database consisting of full-length sequences which are contained in the "all alpha" and "all beta" classes of the SCOP database was employed. The database comprised 120 sequences with a total of 18,885 amino acids. Composite descriptors exemplary of composite descriptor 222, 224 and 226 were employed. Any region in the database that was identified by a composite descriptor gave rise to $R_i$ mislabeled amino acid positions. Table 2, below, shows the ratio of correctly labeled positions for several combinations of the LogProb$_{thres}$ and of the minimum required number, P, of patterns that had to match a region before the region was reported.

TABLE 2

| Minimum number P of patterns required to match a region | LogProb$_{thres}$ choices for the patterns forming the composite descriptors | | | | |
|---|---|---|---|---|---|
| | −23 | −24 | −25 | −26 | −27 |
| 1 | 95.33% | 96.07% | 96.89% | 97.46% | 98.23% |
| 2 | 97.00% | 97.81% | 98.56% | 99.01% | 99.26% |
| 3 | 97.91% | 98.54% | 99.09% | 99.50% | 99.68% |
| 4 | 98.34% | 99.14% | 99.47% | 99.64% | 99.85% |
| 5 | 98.69% | 99.42% | 99.59% | 99.78% | 99.88% |

As can be seen from Table 2, a choice of P equal to five and a LogProb$_{thres}$ equal to −27 resulted in the correct labeling of 99.88% of the processed sequence positions (an equivalent false positive rate of 0.12%). Thus, a choice of P equal to five and a value for LogProb$_{thres}$ between −27 and −25 is appropriate for obtaining an error rate that is less than 0.5%.

The tests run with composite descriptors exemplary of composite descriptor 222, 224 and 226 indicate that the composite descriptor for each category can correctly characterize all of the training sequence fragments for that category. With the assumption that the training sets provide a representative sample of non-canonical elements, the tests indicate that the sensitivity of each of composite descriptor 222, 224 and 226 would be 100% for their respective category. Given that the patterns comprising the composite descriptors used in the test did not contain any of the training sequences explicitly, correct recognition of all of the training sequences is a non-trivial event, especially since the patterns appeared two or more times in the training sequences from each category. Preferably, positions of the query sequence identified by any of composite descriptor 222, 224 or 226 are then labeled as belonging to a particular category. Labeling efforts are confounded when a particular query position is identified by more than one of composite descriptors 222, 224 and 226. To cope with these competing labeling attempts, the symbols $x_1$, $x_2$ and $x_3$ are used to denote the amounts contributed to a query position from each of composite descriptor 222, 224 and 226, respectively. The unit vector $(u_1, u_2, u_3) = (x_1, x_2, x_3)/\|(x_1, x_2, x_3)\|$ is then used to determine the membership of a complex query position in a particular category. For example, if i, j and k represent the categories π-like helices, $3_{10}$-like helices and proline-induced kinks, respectively, then the following are typical thresholding choices used to label complex query positions that were matched by at least P patterns:

(a) if for a position, $u_i$ greater than or equal to 2.5 $u_j$ and $u_i$ greater than or equal to 2.5 $u_k$, the position would be labeled by category i (π-like helices) (similarly for the other categories);

(b) if for a position, $u_i$ greater than or equal to 2.5 $u_k$ and $u_j$ greater than or equal to 2.5 $u_k$, the position would be labeled as a hybrid between categories i and j (π-like helices and $3_{10}$-like helices) (similarly for the other pairs of categories). An example of such a situation is an amino acid that is the signature residue for one non-canonical conformation but also participates in an instance of a second non-canonical conformation that immediately follows its position; and, (c) otherwise, the position would be labeled as a hybrid between all three categories (π-like helices, $3_{10}$-like helices and proline-induced kinks).

Exemplary System

Turning now to FIG. 3, a block diagram is shown of an apparatus 300 for identifying a region in a query sequence corresponding to a non-canonical protein conformation in accordance with one embodiment of the present invention. It should be understood that apparatus 300 represents one embodiment for implementing system 200 of FIG. 2. Apparatus 300 comprises a computer system 310 and removable media 350. Computer system 310 comprises a processor 320, a network interface 325, a memory 330, a media interface b 335 and an optional display 340. Network interface 325 allows computer system 310 to connect to a network, while media interfaces 335 allows computer system 310 to interact with media such as a hard drive or removable media 350.

As is known in the art, the methods and apparatus discussed herein may be distributed as an article of manufacture that itself comprises a machine readable medium containing one or more programs which when executed implement embodiments of the present invention. For instance, the machine readable medium may contain a program configured to form a composite pattern descriptor for sequence patterns corresponding to instances of non-canonical protein conformations; and use the composite pattern descriptor to identify positions of a query sequence corresponding to the sequence patterns. The machine readable medium may be a recordable medium (e.g., floppy disks, hard drive, optical disks such as removable media 350, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used.

Processor 320 can be configured to implement the methods, steps, and functions disclosed herein. The memory 330 could be distributed or local and the processor 320 could be distributed or singular. The memory 330 could be implemented as an electrical, magnetic or optical memory, or any combination of these or other types of storage devices. Moreover, the term "memory" should be construed broadly enough to encompass any information able to be read from or written to an address in the addressable space accessed by processor 320. With this definition, information on a network, accessible through network interface 325, is still within memory 330 because the processor 320 can retrieve the information from the network. It should be noted that each distributed processor that makes up processor 320 generally contains its own addressable memory space. It should also be noted that some or all of computer system 310 can be incorporated into an application-specific or general-use integrated circuit.

Optional video display 340 is any type of video display suitable for interacting with a human user of apparatus 300. Generally, video display 340 is a computer monitor or other similar video display.

EXAMPLES

Figure 4:
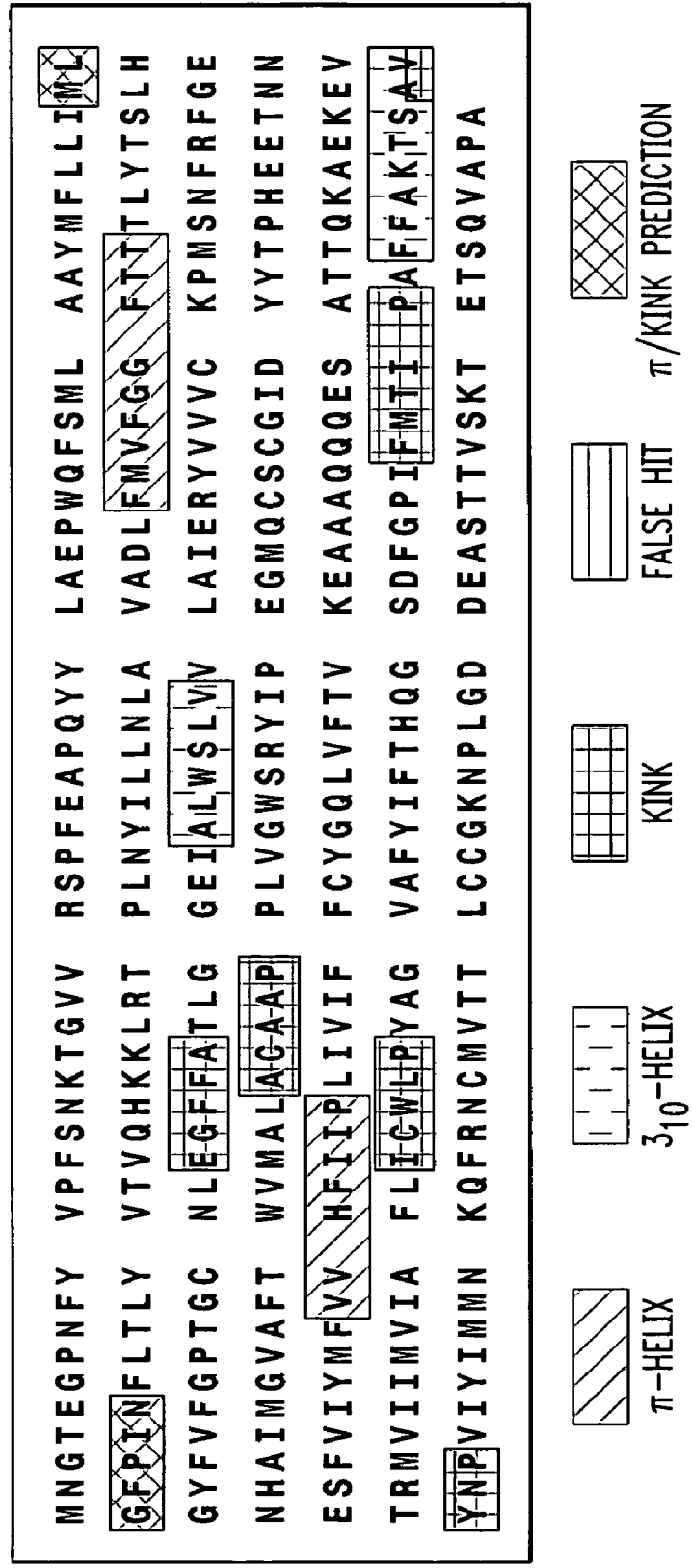
FIG. 4 is a diagram illustrating experimental results of non-canonical conformation identification.

Experiments were conducted with bovine rhodopsin sequence fragments. By setting P equal to five and LogProb$_{thres}$ equal to −25 a complete and correct identification and labeling of all the non-canonical elements is achieved. The results are shown in FIG. 4, wherein the non-canonical features, π-like helices, $3_{10}$-like helices, and proline- or non-proline-induced kink, as well as complex segments containing conformational features of both proline-induced kinks and π-like helices, are indicated by different hatching schemes defined in the legend of FIG. 4. The ability to detect complex segments is notable since such motifs are not present in the training set sequences.

Figure 5:
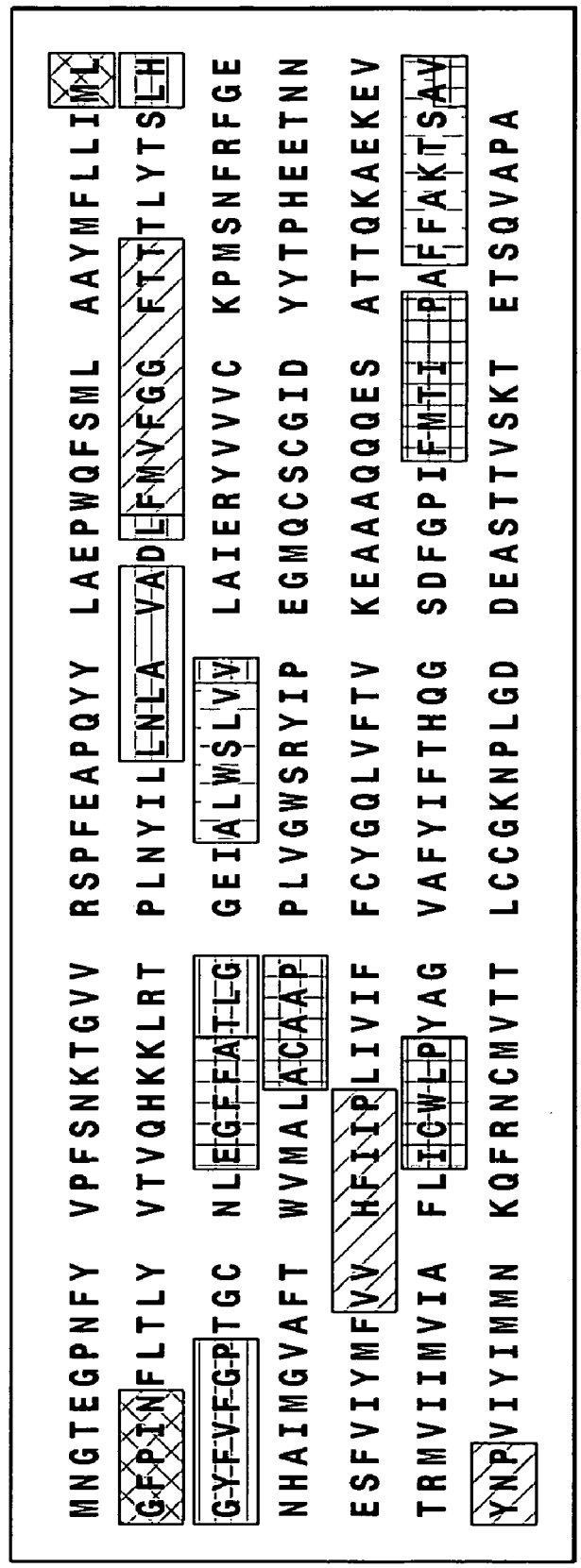
FIG. 5 is a diagram illustrating the impact of parameter settings on experimental results.

Finally, the impact of the parameter settings on the non-canonical conformations identified by our pattern-based search engine are examined through processing of the bovine rhodopsin sequence. Specifically, the effects of reducing the system's stringency, i.e., by increasing LogProb$_{thres}$ from −25 to −23, yet maintaining the value of P at five, are observed. Increasing the system's stringency increases the expected amount of mislabeling. A review of FIG. 5 and the accompanying legend of FIG. 5 reveals that the impact of these more lenient parameter choices on the bovine rhodopsin sequence model generates some false predictions.

It is to be appreciated that the inventive concepts described herein may be implemented on a network such as, for example, the Internet, in a client-server relationship. This allows a user to enter a query sequence at a client device at a remote location that is transmitted to a server over the network and processed at the server. The server then returns the results of the search to the client device of the user via the network.

It is to be understood that the embodiments and variations shown and described herein are merely illustrative of the principles of this invention and that various modifications may be implemented by those skilled in the art without departing from the scope and spirit of the invention.

What is claimed is:

1. A computer-implemented method for determining whether a one-dimensional amino acid query sequence encodes an instance of one of three types of deviations from α-helicity, wherein the three types of deviations from α-helicity comprise three non-canonical helical conformations, wherein the three non-canonical helical conformations are π-helices, $3_{10}$-helices, and kinks, wherein the kinks comprise proline-induced kinks and non proline-induced kinks, comprising the following steps:

providing a system, wherein the system comprises a suitably programmed computer comprising distinct software modules, each of the distinct software modules being embodied on a tangible computer-readable recordable storage medium, and wherein the distinct software modules comprise a composite descriptor module, and an amino acid query sequence processing module, and wherein the system executes the following steps via the suitably programmed computer;

forming three composite pattern descriptors from one-dimensional amino acid sequence patterns identified using pattern-discovery means by processing instances of one-dimensional amino acid sequences that are known to form non-canonical helical conformations belonging to each of π-helices, $3_{10}$-helices, and kinks, respectively, wherein each instance is a one-dimensional amino acid sequence fragment that is known to form a π-helix, $3_{10}$-helix, or a kink in three dimensions, and wherein individual amino acids comprise classes wherein amino acids within each class are permitted to replace each other within the same class, and wherein forming three composite pattern descriptors is carried out by the composite descriptor module executing on a hardware processor;

comparing each composite pattern descriptor with the one-dimensional amino acid query sequence, wherein the query sequence is derived directly from a fragment of rhodopsin, wherein the fragment of rhodopsin comprises a contiguous seciuence of amino acids derived directly from rhodopsin, to determine whether one or more amino acid sequence patterns that form the three composite pattern descriptors have an instance in the one-dimensional amino acid query sequence, wherein comparing each composite pattern descriptor with the one-dimensional amino acid query sequence is carried out by the amino acid query sequence processing module executing on a hardware processor;

using said instances to determine whether the one-dimensional amino acid query sequence encodes an instance of one of the three types of deviations from α-helicity, wherein using said instances to determine whether the one-dimensional amino acid query sequence encodes an instance of one of the three types of deviations from α-helicity is carried out by the amino acid query sequence processing module executing on a hardware processor;

labeling identified positions of the one-dimensional amino acid query sequence as forming a particular non-canonical protein structure, wherein the particular non-canonical protein structure will be formed by the amino acid seciuence that contains the one-dimensional amino acid query sequence, wherein labeling the identified positions of the one-dimensional amino acid query sequence is carried out by the amino acid query sequence processing module executing on a hardware processor, wherein $|x_1|/\sqrt{(x_1^2+x_2^2+x_3^2)}$, $|x_2|/\sqrt{(x_1^2+x_2^2+x_3^2)}$ and $|x_3|/\sqrt{(x_1^2+x_2^2+x_3^2)}$ are used to determine the label of each individual amino acid of the one-dimensional query sequence in a Π-helix, $3_{10}$-helix, or kink non-canonical category, and $X_1$, $x_2$ and $x_3$ represent amounts assigned to each individual amino acid of the query sequence, and wherein:

the individual amino acid of the one-dimensional query seciuence would be labeled as belonging to a π-helix category if for the individual amino acid, $|x_1|/\sqrt{(x_1^2+x_2^2+x_3^2)}$ is geater than or equal to 2.5 times $|x_2|/\sqrt{(x_1^2+x_2^2+x_3^2)}$ and greater than or equal to 2.5 times $|x_3|/\sqrt{(x_1^2+x_2^2+x_3^2)}$;

the individual amino acid of the one-dimensional query sequence would be labeled as belonging to a $3_{10}$-helix category if for the individual amino acid, $|x_2|/\sqrt{(x_1^2+x_2^2+x_3^2)}$ is greater than or equal to 2.5 times $|x_1|/\sqrt{(x_1^2+x_2^2+x_3^2)}$ and greater than or equal to 2.5 times $|x_3|/\sqrt{(x_1^2+x_2^2+x_3^2)}$;

the individual amino acid of the one-dimensional query seciuence would be labeled as belonging to a [a] kink category if for the individual amino acid, $|x_3|/\sqrt{(x_1^2+x_2^2+x_3^2)}$ is greater than or equal to 2.5 times $|x_1|/\sqrt{(x_1^2+x_2^2+x_3^2)}$ and greater than or equal to 2.5 times $|x_1|/\sqrt{(x_1^2+x_2^2+x_3^2)}$;

the individual amino acid of the one-dimensional query sequence would be labeled as a hybrid between a π-helix category and a $3_{10}$-helix category if for the individual amino acid, $|x_1|/\sqrt{(x_1^2+x_2^2+x_3^2)}$ is greater than or equal to 2.5 times $|x_3|/\sqrt{(x_1^2+x_2^2+x_3^2)}$ and $|x_2|/\sqrt{(x_1^2+x_2^2+x_3^2)}$ is greater than or equal to 2.5 times $|x_3|/\sqrt{(x_1^2+x_2^2+x_3^2)}$;

the individual amino acid of the one-dimensional query sequence would be labeled as a hybrid between a π-helix category and a kink category if for the individual amino acid $|x_1|/\sqrt{(x_1^2+x_2^2+x_3^2)}$ is greater than or equal to 2.5 times $|x_2|/\sqrt{(x_1^2+x_2^2+x_3^2)}$ and $|x_3|/\sqrt{(x_1^2+x_2^2+x_3^2)}$ is greater than or equal to 2.5 times $|x_2|/\sqrt{(x_1^2+x_2^2+x_3^2)}$;

the individual amino acid of the one-dimensional query seciuence would be labeled as a hybrid between a $3_{10}$-helix category and a kink category if for the individual amino acid, $|x_2|/\sqrt{(x_1^2+x_2^2+x_3^2)}$ is greater than or equal to 2.5 times $|x_2|/\sqrt{(x_1^2+x_2^2+x_3^2)}$ and $|x_3|/\sqrt{(x_1^2+x_2^2+x_3^2)}$ is greater than or equal to 2.5 times $|x_1|/\sqrt{(x_1^2+x_2^2+x_3^2)}$; and the individual amino acid of the one-dimensional query sequence would be otherwise labeled as a hybrid between all three non-canonical categories; and outputting said determination to a user, wherein outputting said determination to a user is carried out by the amino acid query sequence processing module executing on a hardware processor.

2. The method of claim 1, wherein the step of forming three composite pattern descriptors from one-dimensional amino acid sequence patterns comprises selecting those patterns wherein a residue at a fixed position coincides with a signature amino acid residue, wherein the step of selecting those patterns is carried out by the composite descriptor module executing on a hardware processor.

3. The method of claim 1, wherein a number of one-dimensional sequence patterns are used to form the composite pattern descriptors, and the number of one-dimensional sequence patterns used is determined by an estimated probability value for each pattern.

4. The method of claim 1, wherein the one-dimensional amino acid sequence fragments used to derive the one-dimensional amino acid sequence patterns comprise examples of one-dimensional amino acid sequences that are known to form a respective non-canonical conformation.

5. The method of claim 1, further comprising sub-selecting one-dimensional amino acid sequence patterns, wherein the amino acid sequence patterns each comprise about seven to about nine amino acid residues, wherein sub-selecting one-dimensional amino acid sequence patterns is carried out by the composite descriptor module executing on a hardware processor.

6. The method of claim 1, wherein searching is conducted through use of a search engine comprising the composite pattern descriptors, and wherein the step of searching is carried out by the amino acid query sequence processing module executing on a hardware processor.

7. The method of claim 1, wherein an amino acid class comprises: {A,G}, {D,E}, {K,R}, {I,L,M,V}, {S,T}, {Q,N} and {F,Y}.

8. The method of claim 1, wherein the one-dimensional amino acid sequence patterns comprise wild card positions with each wild card position replaced by a regular expression of the type $\{X_1 X_2 \ldots X_N\}$, wherein each $X_i$ is an amino acid represented by the wild card, and N is a maximal number of amino acids.

9. The method of claim 8, wherein those patterns with a number of amino acids greater than or equal to N are discarded.

10. The method of claim 9, wherein N is seven.

11. The method of claim 1, wherein the positions of the one-dimensional amino acid query sequence corresponding to sequence patterns are assigned an amount.

12. The method of claim 11, wherein the positions are labeled with $x_1$, $x_2$ and $x_3$ to denote the amounts assigned.

* * * * *